(12) United States Patent
Moretti

(10) Patent No.: US 8,268,895 B2
(45) Date of Patent: Sep. 18, 2012

(54) PERFUMING INGREDIENTS OF THE FLORAL AND/OR ANIS TYPE

(75) Inventor: Robert Moretti, Grand-Lancy (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 13/123,147

(22) PCT Filed: Nov. 3, 2009

(86) PCT No.: PCT/IB2009/054865
§ 371 (c)(1),
(2), (4) Date: Apr. 7, 2011

(87) PCT Pub. No.: WO2010/052636
PCT Pub. Date: May 14, 2010

(65) Prior Publication Data
US 2011/0229426 A1    Sep. 22, 2011

(30) Foreign Application Priority Data

Nov. 7, 2008   (WO) .................. PCT/IB2008/054663

(51) Int. Cl.
  A61K 8/30   (2006.01)
  A61K 8/02   (2006.01)
  A61K 8/00   (2006.01)
  A61Q 5/00   (2006.01)
  A61Q 15/00  (2006.01)
  A61Q 19/10  (2006.01)
  A61Q 13/00  (2006.01)
  A61L 9/00   (2006.01)

(52) U.S. Cl. ........ 514/701; 514/703; 514/764; 424/401; 424/65; 424/70.1; 424/73

(58) Field of Classification Search .................. None
See application file for complete search history.

(56) References Cited

U.S. PATENT DOCUMENTS

| | | | | |
|---|---|---|---|---|
| 3,694,232 A | * | 9/1972 | Hall et al. ...................... | 426/538 |
| 3,879,425 A | | 4/1975 | Hall et al. ................... | 260/340.9 |
| 5,486,502 A | * | 1/1996 | Sprecker et al. ................ | 512/21 |

OTHER PUBLICATIONS

International Search Report and Written Opinion mailed Jan. 15, 2010 for Application No. PCT/IB2009/054865 filed Nov. 3, 2009.
Boldrini et al., "Palladium Catalyzed Allylation of Reformatsky Reagents. Synthesis of γ,δ-Unsaturated Esters," Tetrahedron Letters, 27(35):4223-4226 (1986).
Carfagna et al., "The Regio- and Stereoselectivities of the Reaction of Allyl Acetates and Silyl Ketene Acetals Catalyzed by Pd(0) Complexes: A New Route to Cyclopropane Derivatives," J. Org. Chem., 56:3924-3927 (1991).
Gao et al., "An Unusual β-Vinyl Effect Leading to High Efficiency and Enantioselectivity of the Amidase, Nitrile Biotransformations for the Preparation of Enantiopure 3-Arylpent-4-enoic Acids and Amides and Their Applications in Synthesis," J. Org. Chem., 71:9532-9535 (2006).
Gladiali et al., "Rearrangement of diallyl ethers catalyzed by $H_4Ru_4(CO)_8[(-31\ )-DIOP]_2$," La Chimica e L'Industria, 63(7-8):506-511 (1981).
Kerrigan et al., "Pd(II)-catalyzed aliphatic Claisen rearrangements of acyclic allyl vinyl ethers," Tetrahedron, 64:6863-6869 (2008).
Maruoka et al., "Virtually Complete Blocking of α,β-Unsaturated Aldehyde Carbonyls by Complexation with Aluminum Tris(2,6-diphenylphenoxide)," J. Am. Chem. Soc., 116:4131:4132 (1994).
May et al., "Non-Carbonyl-Stabilized Metallocarbenoids in Synthesis: The Development of a Tandem Rhodium-Catalyzed Bamford-Stevens/Thermal Aliphatic Claisen Rearrangement Sequence," J. Am. Chem. Soc., 124:12426-12427 (2002).
Muraoka et al., "First Asymmetric Synthesis of (−)-Sugiresinol Dimethyl Ether," Tetrahedron Asymmetry, 2(5):357-358 (1991).

* cited by examiner

Primary Examiner — Fereydoun G Sajjadi
Assistant Examiner — Alma Pipic
(74) Attorney, Agent, or Firm — Winston & Strawn LLP

(57) ABSTRACT

The present invention concerns the use as perfuming ingredient, for instance to impart odor notes of the floral and/or green type, of a compound of formula 5 wherein R is an ortho, meta or para substituent of the phenyl, and represents a hydrogen atom or a C 1-2 alkyl or alkoxyl group; R 1 represents a hydrogen atom or a methyl or ethyl group; 10 R 2 represents a hydrogen atom or a C 1-3 alkyl group; and X represents a CHO, COOR 3, CH(OR 4) 2 or CN group, R 3 being a methyl or ethyl group, and R 4, taken seperately, being a methyl or ethyl group, or said R 4, taken together, a C 2-5 alkanediyl group; and at least one of said R, R 1 or R 2 represents a group containing at least one carbon atom.

(I)

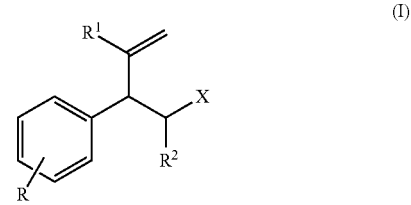

8 Claims, No Drawings

PERFUMING INGREDIENTS OF THE FLORAL AND/OR ANIS TYPE

This application is a 371 filing of International Patent Application PCT/IB2009/054865 filed Nov. 3, 2009.

TECHNICAL FIELD

The present invention relates to the field of perfumery. More particularly, it concerns a $C_{12}$ to $C_{17}$ substituted derivative of 3-phenyl-4-pentenal.

The present invention concerns also the use of said compound in the perfumery industry as well as the compositions or articles containing said compound, and some of said compounds.

PRIOR ART

To the best of our knowledge, none of the invention's compounds has been described as perfuming ingredients.

Amongst the invention's compounds only two are known in the prior art, 4-methyl-3-phenyl-4-pentenal (see K. Maruoka et al, in *J.A.C.S*, 1994, 116, 4131) and 2,4-dimethyl-3-phenyl-4-pentenal (see S. Gladiali et al, in *Chimica e Industria*, 1981, 63, 506). Both compounds are disclosed as simple chemical compounds and none of these documents anticipates the use of said compounds as perfuming ingredients.

To the best of our knowledge, amongst the known perfuming ingredients, none can be considered as a close structural analogue.

DESCRIPTION OF THE INVENTION

We have now surprisingly discovered that a compound of formula

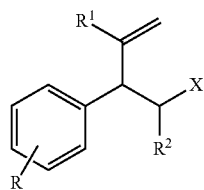

(I)

wherein R is an ortho, meta or para substituent of the phenyl, and represents a hydrogen atom or a $C_{1-2}$ alkyl or alkoxyl group;
$R^1$ represents a hydrogen atom or a methyl or ethyl group;
$R^2$ represents a hydrogen atom or a $C_{1-3}$ alkyl group; and
X represents a CHO, $COOR^S$, $CH(OR^4)_2$ or CN group, $R^3$ being a methyl or ethyl group, and $R^4$, taken seperately, being a methyl or ethyl group, or said $R^4$, taken together, a $C_{2-5}$ alkanediyl group; and
at least one of said R, $R^1$ or $R^2$ represents a group containing at least one carbon atom; can be used as perfuming ingredient, for instance to impart odor notes of the floral and/or green type.

According to a particular embodiment of the invention, said invention's compounds are those having 12, 13 or 14 carbon atoms in total, preferably it is a $C_{13-14}$ compound.

According to a particular embodiment of the invention, said invention's compounds are those wherein one of the $R^1$ and $R^2$ is a methyl group and the other is a hydrogen atom or a methyl group.

According to a particular embodiment of the invention, said invention's compounds are those wherein at least two of said R, $R^1$ or $R^2$ represent a group containing at least one carbon atom.

According to a particular embodiment of the invention, said compounds (I) are those wherein R is an ortho, meta or para substituent of the phenyl ring and represents a hydrogen atom or a methoxy, methyl or ethyl group;
$R^1$ represents a methyl or ethyl group; and
$R^2$ represents a hydrogen atom or a methyl or ethyl group;
X represents a CHO, $COOR^3$ or CN group, $R^3$ being a methyl or ethyl group.

According to any one of the above embodiments of the invention, said compounds (I) are those wherein R is an ortho, meta or para substituent of the phenyl ring and represents a methoxy, methyl or ethyl group.

According to any one of the above embodiments of the invention, said compounds (I) are those wherein the R group is methyl or ethyl group.

According to any one of the above embodiments of the invention, said compounds (I) are those wherein the R group is a para, meta or ortho substituent, and in particular is a para or meta substituent, or of a mixture thereof. According to any one of the above embodiments of the invention, said compounds (I) are those which are in the form of mixture of para or meta isomers and the para isomer accounts for at least 90% w/w of said mixture, or even at least 95%.

According to any of the above embodiments of the invention, said invention's compounds are those wherein X represents a CHO group.

To the best of our knowledge, the compounds of formula (I) wherein X is a CHO or a CN group are new and are therefore an object of the present invention, at the exception of the two cited above.

According to a particular embodiment of the invention, said novel compounds are those wherein R is an ortho, meta or para, in particular a para, substituent of the phenyl ring and represents a methyl or methoxy group, $R^1$ represents a methyl or ethyl group, $R^2$ represents a hydrogen atom or a methyl or ethyl group, and X represents a CHO group.

It is also understood that, according any of the above embodiments, said compound (I) can be in the form of any one of its stereoisomers or of a mixture thereof.

As specific examples of the invention's compounds, one may cite, as non-limiting example, 2,4-dimethyl-3-(4-methylphenyl)-4-pentenal, which possesses an aldehydic, floral (marguerite), powdery-anis odor character, with a fruity-hexenal-apple aspect. This compound imparts also interesting bottom notes of the anis, aromatic (basil), verbena, green and very aldehydic notes type.

Although having a quite different chemical structure, said compound imparts an odor which can be considered as being in between the one imparted by the known perfuming ingredients 3-(4-methoxyphenyl)-2-methylpropanal and 3-(1,3-benzodioxol-5-yl)-2-methylpropanal. However, the invention's compound is more powerful and substantive than the two cited known ingredients, and allows new olfactive effects as shown in the Examples.

This compound represents an embodiment of the invention particularly appreciated by the perfumers.

As other example, one may cite 4-methyl-3-(4-methylphenyl)-4-pentenal, which possesses a green, floral and anis odor. Its odor is in between the one of Trifernal® (trademark to Firmenich SA: 3-phenylbutanal) and the one of 2,4,6-trimethyl-3-cyclohexene-1-carbaldehyde (Arctander N° 761) with in addition an carvone, anis note. This invention's compound possesses a very substantive odor.

As other specific, but non-limiting, examples of the invention's compounds, one may cite the following ones in Table 1:

TABLE 1

Invention's compounds and their odor properties

| Compound structure and name | Odor notes |
|---|---|
| 2,4-dimethyl-3-phenyl-4-pentenal | Green, carvone, linalyl, aldehydic |
| 2-methyl-3-phenyl-4-pentenal | Green, fruity and floral |
| 2-ethyl-3-phenyl-4-pentenal | Orange flower, green, and rosy-fruity bottom notes |
| Methyl 4-methyl-3-phenyl-4-pentenoate | Rosy, green |
| 4-methyl-3-phenyl-4-pentenal | Green, very natural |
| 3-(2-methoxyphenyl)-2-methyl-4-pentenal | Green, aldehydic |

TABLE 1-continued

Invention's compounds and their odor properties

| Compound structure and name | Odor notes |
|---|---|
| 4-methyl-3-phenyl-4-pentenenitrile | Green, nitrile |
| 4-methyl-3-(4-methylphenyl)-4-pentenenitrile | Green, nitrile |

According to a particular embodiment of the invention the compounds of formula (I) are: 2,4-dimethyl-3-(4-methylphenyl)-4-pentenal or 4-methyl-3-(4-methylphenyl)-4-pentenal, as well as 4-methyl-3-phenyl-4-pentenal.

As can be seen from the above table, although the precise tonalities of the invention's compounds may vary according to the exact structure of the compounds, notes of the green and/or floral types are characteristic. When R is a methyl group and X is a CHO group, the compound (I) possesses also an anisic note quite appreciated.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

For the compositions which comprise both a perfumery carrier and a perfumery base, other suitable perfumery carrier, than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company).

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:
i) as perfuming ingredient, at least one compound of formula (I), as defined above, or an invention's perfuming composition; and
ii) a consumer product base;
is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric softeners, fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. Concentrations lower than these, such as in the order of 0.01% to 1% by weight, can be used when these compounds are incorporated into perfumed articles, percentage being relative to the weight of the article.

The invention's compounds can be prepared according to a method comprising the preparation of an ester of the invention, which can be converted into an alcohol by reduction, and finally the oxidation of said alcohol into an invention's aldehyde. The aldehyde can be subsequently be transformed into an acetal or cyanide according to the invention using standard methods known from the art. The ester itself can be prepared by reacting an appropriate orthoester with an appropriate allyl-benzyl alcohol, under Claisen rearrangement conditions, as show in the scheme herein below:

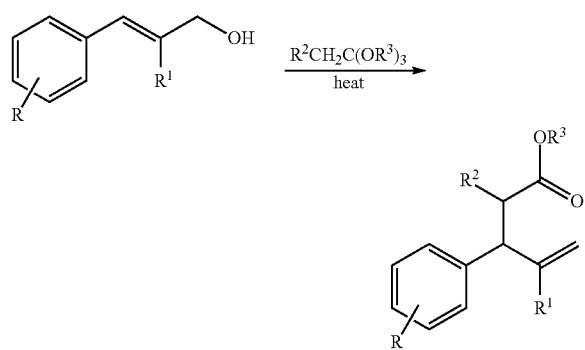

Using such methodology, the alcohols and esters according to the invention are also valuable intermediates for the production of the aldehydes and cyanides of formula (I).

Alternatively, the invention's compounds can be obtained by a process comprising the following key steps:

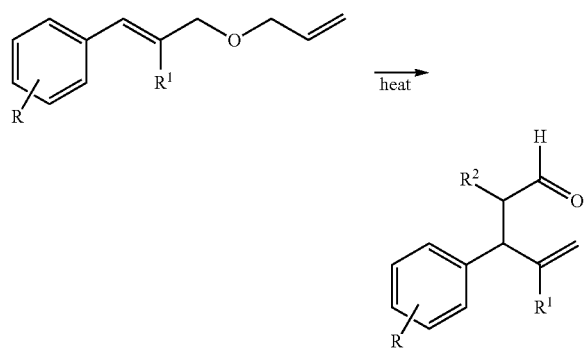

The aldehyde can be then transformed into the desired invention's compound using standard methods.

Examples of all said methodologies are provided herein below in the Examples.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical shifts δ are indicated in ppm with respect to TMS as standard, the coupling constants J are expressed in Hz.

Example 1

Synthesis of Compounds of Formula (I)

1-[(1E)-3-(Allyloxy)-2-methyl-1-propenyl]-4-methylbenzene

Solid potassium tert-butylate (47 g, 0.411 mol) was added portion-wise to a solution of E-3-(4-methylphenyl)-2-methyl-2-propen-1-ol (68.05 g, 0.420 mol) in dry THF (800 ml) at room temperature under nitrogen (exothermic to 30° C.). After 1 more hour at room temperature, the reaction was cooled to 5° C. and tetra butyl ammonium iodide (7.9 g, 0.021 mol) was added followed by allyl bromide (102.65 g, 0.840 mol) drop-wise. The reaction was warmed up to room temperature overnight and poured onto water (800 ml). The reaction was extracted twice with ethyl acetate. Each organic phase was washed with water and brine. Combined extracts were dried over solid anhydrous sodium sulfate. The solid was filtered off, rinsed with diethyl ether and the solvents were removed under vacuum. The product was purified by distillation under vacuum through a 20-cm Widmer column. 79 g of the desired product were obtained (yield=93%). B.P.=82° C./0.001 mbar $^{13}C$-NMR: 136.07 (s), 134.91 (d), 134.66 (s), 134.38 (s), 128.82 (d), 126.89 (d), 116.90 (t), 76.39 (t), 70.78 (t), 21.14 (q), 15.51 (q).

$^1H$-NMR: 7.15 (m, 4H), 6.47 (s, 1H), 6.00-5.90 (m, 1H), 5.30 (m, 1H), 5.18 (m, 1H), 4.00 (m, 4H), 2.32 (s, 3H), 1.88 (s, 3H).

2,4-Dimethyl-3-(4-methylphenyl)-4-pentenal

The 1-[(1E)-3-(Allyloxy)-2-methyl-1-propenyl]-4-methylbenzene (72.7 g, 0.359 mol), [$RuCl_2(PPh_3)_3$] (1.1 g), BHT (50 mg) and benzene (250 ml) were heated together in an autoclave placed in an oil bath at 165-170° C. for 24 hours. After cooling to room temperature, the benzene was evaporated under vacuum and the residue chromatographed on silica gel (eluent: heptanes/ethyl acetate 25:1 to 4:1), then distilled under vacuum through a 20-cm Widmer column. 21.3 g of the desired product were obtained (yield=29%) as a 40:60 mixture of diastereoisomers. B.P.=95° C./0.001 mbar $^{13}C$-NMR: 204.49 (s), 204.39 (s), 146.40 (s), 144.99 (s), 137.33 (s), 137.03 (s), 136.47 (s), 129.26 (d), 129.21 (d), 128.25 (d), 128.04 (d), 112.57 (t), 111.72 (t), 54.70 (d), 54.00 (d), 48.44 (d), 47.06 (d), 22.00 (q), 21.01 (q), 20.97 (q), 19.64 (q), 13.38 (q), 13.34 (q).

$^1H$-NMR: 9.62 (d, J=2.5, 0.4H), 9.42 (d, J=2.5, 0.6H), 7.12-7.05 (m, 4H), 4.97-4.82 (m, 2H), 3.42 (d, J=11.5, 0.6H), 3.32 (d, J=11.5, 0.4H), 3.04-2.88 (m, 1H), 2.34 (s, 1.2H), 2.28 (s, 1.8H), 1.63 (s, 1.2H), 1.47 (s, 1.8H), 1.09 (d, J=7, 1.8H), 0.87 (d, 1.2H).

4-Methyl-3-(4-methylphenyl)-4-pentenal (3E)-(4-Methylphenyl)-2-methyl-2-propen-1-ol (17.33 g, 0.102 mol), tri (ethylene glycol) divinyl ether (Aldrich 98%, 20.5 g, 0.102 mol) and mercury(II) acetate (1 g, 0.003 mol) were heated together under nitrogen at 155-160° C. (bath temperature) for 3 hours. After cooling to room temperature, the reaction was diluted with heptanes, washed with water (3 times). Each aqueous phase was re-extracted with heptanes. Combined extracts were dried over solid anhydrous sodium sulfate. The solid was filtered off, rinsed with heptanes and the solvent was removed under vacuum. The crude product was purified by column chromatography on silica gel (eluent: heptanes/ethyl acetate (11:1) followed by bulb-to-bulb distillation (81° C./0.002 mbar). 8.71 g of the desired product were obtained (yield=43%).

$^{13}$C-NMR: 201.61 (d), 146.48 (s), 138.67 (s), 136.39 (s), 129.31 (d), 127.53 (d), 111.03 (t), 47.60 (t), 46.28 (d), 21.48 (q), 20.99 (q).

$^{1}$H-NMR: 9.68 (t, J=2.5, 1H), 7.12 (s, 4H), 4.90 (broad s, 1H), 4.86 (broad s, 1H), 3.80 (t, J=7.5, 1H), 2.93-2.73 (m, 2H), 2.32 (s, 3H), 1.62 (s, 3H).

Methyl 4-methyl-3-phenyl-4-pentenoate

3-Phenyl-2-methyl-2-propen-1-ol (50 g, 0.32 mol) and trimethyl orthoacetate (263 g, 2.2 mol) were heated together in the presence of propionic acid (0.3 ml) in a bath at 145° C. for 6 hours, while distilling the methanol formed during the reaction. After removing the residual methanol and the excess orthoacetate under vacuum, the product was purified by distillation through a 20-cm Widmer column. 80 g of the desired product were obtained (yield=78%). B.P.=55° C./0.001 mbar $^{13}$C-NMR: 172.56 (s), 146.67 (s), 141.99 (s), 128.46 (d), 127.65 (d), 126.71 (d), 110.46 (t), 51.56 (q), 48.52 (t), 39.10 (t), 21.63 (q).

$^{1}$H-NMR: 7.30-7.15 (m, 5H), 4.91 (broad s, 1H), 4.88 (broad s, 1H), 3.80 (t, J=7.5, 1H), 3.58 (s, 3H), 2.87 (dd, $J_1$=9, $J_2$=15, 1H), 2.70 (dd, $J_1$=9, $J_2$=15, 1H), 1.61 (s, 3H).

4-Methyl-3-phenyl-4-penten-1-ol

The methyl 4-methyl-3-phenyl-4-pentenoate (258.3 g, 1.251 mol) was added, at 0° C. under nitrogen, to lithium aluminum hydride (25 g, 0.625 mol) in dry THF (1 liter), drop-wise. After 30 minutes, the cooling bath was removed and the reaction allowed reaching room temperature. After 24 h, more THF (1 liter) was added and the reaction was cooled to 0° C. and treated successively with water (25 ml), 5% aqueous sodium hydroxide (75 ml) and water (25 ml). The reaction was stirred at room temperature for 30 minutes. Anhydrous solid sodium sulfate was added (100 g) and stirring continued for 5 minutes The solid was filtered off, rinsed with diethyl ether and the filtrate was evaporated under vacuum. The product was purified distillation through a 20-cm Widmer column. 214 g of the desired product were obtained (yield=97%).

$^{13}$C-NMR: 147.77 (s), 142.99 (s), 128.35 (d), 127.81 (d), 126.38 (d), 110.50 (t), 61.16 (t), 48.96 (d), 35.71 (t), 20.99 (q).

$^{1}$H-NMR: 7.35-7.15 (m, 5H), 4.93 (broad s, 1H), 4.84 (broad s, 1H), 3.62-3.50 (m, 2H), 3.38 (t, J=7.5, 1H), 2.15-2.07 (m, 1H), 1.98-1.90 (m, 1H), 1.78 (broad t, 1H), 1.55 (s, 3H).

4-Methyl-3-phenyl-4-pentenal

Solid pyridinium chlorochromate (110.24 g, 0.5 mol) was added portion-wise to a pre-cooled (−10° C.) mixture of 4-methyl-3-phenyl-4-penten-1-ol (70 g, 0.418 mol) and anhydrous sodium acetate (41.5 g, 0.5 mol) in dry dichloromethane (400 ml) under nitrogen. After 30 minutes, the reaction was warmed up to room temperature. After 4 hours, diethyl ether (1 liter) was added to the reaction. After stirring for 30 minutes, the reaction was filtered through silica gel, rinsing with diethyl ether. The solvent was removed under vacuum and the residue was purified by column chromatography on silica gel (eluent: heptanes/ethyl acetate 25:1 to 5:1) followed by distillation through a 20-cm Widmer column. 24 g (yield=33%) of the desired product were obtained. B.P.=50° C./0.001 mbar.

$^{13}$C-NMR: 201.44 (d), 146.28 (s), 141.71 (s), 128.62 (d), 127.67 (d), 126.84 (d), 111.22 (t), 47.55 (t), 46.63 (d), 21.53 (q).

$^{1}$H-NMR: 9.68 (t, J=2.5, 1H), 7.32-7.25 (m, 2H), 7.24-7.17 (m, 3H), 4.93 (broad s, 1H), 4.89 (broad s, 1H), 3.85 (t, J=7.5, 1H), 2.93 (m, 1H), 2.80 (m, 1H), 1.61 (s, 3H).

(1E)-[3-(allyloxy)-2-methyl-1-propenyl]benzene

Solid potassium tert-butylate (110 g, 0.960 mol) was added portion-wise (1 hour) to a solution of trans-2-methyl-3-phenyl-2-propen-1-ol (100 g, 0.950 mol) in dry THF (1 liter) at room temperature under nitrogen. After 1 more hour at room temperature, the reaction was cooled to 5° C. and tetra butyl ammonium iodide (12.1 g, 0.032 mol) was added followed by allyl chloride (100 g, 1.280 mol) drop-wise. The reaction was warmed up to room temperature overnight and poured onto water (2 liters). The reaction was extracted twice with ethyl acetate. Each organic phase was washed with water and brine. Combined extracts are dried over solid anhydrous sodium sulfate. The solid was filtered off, rinsed with diethyl ether and the solvents were removed under vacuum. The product was purified by distillation through a 20-cm Widmer column. 120.5 g of the desired compound was obtained (97% pure, 0.620 mol, 97%). B.P.=70° C./0.067 mbar $^{13}$C-NMR: 137.56 (s), 135.14 (s), 134.86 (d), 128.90 (d), 128.09 (d), 126.84 (d), 126.42 (d), 116.93 (t), 76.21 (t), 70.84 (t), 15.47 (q).

$^{1}$H-NMR: 7.32-7.15 (m, 5H), 6.52 (s, 1H), 6.02-5.90 (m, 1H), 5.30 (m, 1H), 5.20 (m, 1H), 4.02-3.98 (m, 4H), 1.89 (s, 3H).

2,4-Dimethyl-3-phenyl-4-pentenal

The (1E)-[3-(allyloxy)-2-methyl-1-propenyl]benzene (107.79 g, 0.571 mol), [RuCl$_2$(PPh$_3$)$_3$] (3.13 g), BHT (1 g) and benzene (500 ml) were heated together in an autoclave in an oil bath at 190° C. for 4 hours. After cooling to room temperature, solvents were evaporated and the residue was distilled trough a 20-cm Widmer column to give 85.9 g of the desired compound (0.457 mol, 80%) as a 3:1 mixture of diastereoisomers. B.P.=95° C./0.032 mbar $^{13}$C-NMR (major diastereoisomer): 204.30 (d), 146.20 (s), 140.09 (s), 128.52 (d), 128.17 (d), 126.90 (d), 111.88 (t), 54.34 (d), 48.42 (d), 22.06 (q), 13.39 (q).

$^{1}$H-NMR: 9.62 (d, J=2.5, 0.75H), 9.42 (d, J=2.5, 0.25H), 7.32-7.15 (m, 5H), 4.98-4-87 (m, 2H), 3.48 (d, J=11.5, 0.25H), 3.37 (d, J=11.5, 0.75H), 3.08-2.90 (m, 1H), 1.62 (s, 2.25H), 1.57 (s, 0.75H), 1.12 (d, J=7, 0.75H), 0.87 (d, J=7, 2.25H).

(1E)-3-(21-Butenyloxy)-1-phenyl-1-propene

Sodium hydride (60% in mineral oil, 40 g, 1 mol) was added portion-wise to a solution of cinnamyl alcohol (103 g, 0.75 mol) in dry THF (1 liter) at 5° C. under nitrogen. The reaction was warmed up to room temperature then refluxed. After 30 minutes, tetra butyl ammonium iodide (10 g, 0.027 mol) was added followed by crotyl chloride (100 g, 1.10 mol) over a 1 h-period. The reaction was allowed reaching room temperature overnight, before being poured onto water. The organic phase was washed with water (3 times) and brine. Each aqueous phase was re-extracted with heptanes. Combined extracts were dried over solid anhydrous sodium sulfate. The solid was filtered off, rinsed with heptanes and the solvents were removed under vacuum. The product was purified by distillation through a 20-cm Widmer column. 129.9 g of the desired compound were obtained (0.69 mol, 92%) as a 4:1 mixture of E/Z isomers (crotyl disubstituted double bond). B.P.=87° C./0.001 mbar.

$^{13}$C-NMR (E,E-isomer): 136.80 (s), 132.27 (d), 129.67 (d), 128.51 (d), 127.59 (d), 127.53 (d), 126.46 (d), 126.24 (d), 70.89 (t), 70.48 (t), 17.79 (q).

$^1$H-NMR: 7.37 (m, 2H), 7.30 (m, 2H), 7.22 (m, 1H), 6.60 (m, 1H), 6.32-6.24 (m, 1H), 5.28-5.07 (m, 2H), 4.12 (m, 2H), 3.93 (m, 2H), 1.75-1.65 (m, 3H).

2-Ethyl-3-phenyl-4-pentenal

The (1E)-3-(2'-Butenyloxy)-1-phenyl-1-propene (95 g, 0.505 mol), [RuCl$_2$(PPh$_3$)$_3$] (0.5 g) and BHT (0.5 g) were refluxed under Argon in pseudo-cumene (100 ml) for 1 hour. After cooling to room temperature, the solvent was distilled under vacuum (40° C./5 mbar) and the compound was purified by column chromatography on silica gel (eluent: heptanes/ethyl acetate: 50:1 to 10:1) followed bulb-to-bulb distillation (98° C./1 mbar). 11.4 g of the desired product were obtained (0.060 mol, 12%), as a 1:1 mixture of diastereoisomers.

$^{13}$C-NMR: 204.69 (d), 204.27 (d), 141.26 (s), 141.07 (s), 139.12 (d), 138.70 (d), 128.78 (d), 128.01 (d), 127.89 (d), 126.85 (d), 116.56 (t), 116.24 (t), 57.63 (d), 57.43 (d), 50.63 (d), 50.38 (d), 20.80 (t), 20.60 (t), 11.48 (q), 11.39 (q).

$^1$H-NMR: 9.59 (d, J=2.5, 0.5H), 9.44 (d, J=2.5, 0.5H), 7.35-7.10 (m, 5H), 6.00-5.88 (m, 1H), 5.15-5.05 (m, 2H), 3.55 (q, J=7, 1H), 2.68-2.55 (m, 1H), 1.75-1.30 (m, 2H), 0.90 (t, J=7, 1.5H), 0.80 (t, J=7, 1.5H).

(E)-3-Allyloxy-1-phenyl-1-propene

Sodium hydride (60% in mineral oil, 26 g, 0.60 mol) was added portion-wise to a solution of cinnamyl alcohol (40 g, 0.29 mol) in dry THF (600 ml) at 5° C. under nitrogen. The reaction was warmed up to room temperature then refluxed. After 30 minutes, tetra butyl ammonium iodide (4 g, 0.011 mol) was added followed by allyl chloride (45.6 g, 0.60 mol) over a 1 h-period. The reaction was allowed reaching room temperature overnight, before being poured onto water. The organic phase was washed with water (3 times) and brine. Each aqueous phase was re-extracted with heptanes. Combined extracts were dried over solid anhydrous sodium sulfate. The solid was filtered off, rinsed with heptanes and the solvents were removed under vacuum. The product was purified by bulb-to-bulb distillation (80° C./0.062 mbar). 50 g of the desired compound were obtained (0.287 mol, 99%).

$^{13}$C-NMR: 136.84 (s), 134.86 (d), 132.42 (d), 128.57 (d), 127.67 (d), 126.53 (d), 126.14 (d), 116.97 (t), 71.14 (t), 70.74 (t).

$^1$H-NMR: 7.36 (m, 2H), 7.28 (m, 2H), 7.20 (m, 1H), 6.60 (d, J=16, 1H), 6.28 (td, J$_t$=7, J$_d$=16, 1H), 5.98-5.88 (m, 1H), 5.28 (m, 1H), 5.18 (m, 1H), 4.12 (d, J=7, 2H), 4.00 (m, 2H).

2-Methyl-3-phenyl-4-pentenal

The (E)-3-allyloxy-1-phenyl-1-propene (48.9 g, 0.28 mol) and [RuCl$_2$(PPh$_3$)$_3$] (0.036 g) were refluxed together under Argon in pseudo-cumene (100 ml) for 1 hour. After cooling to room temperature, the solvent was distilled under vacuum (40° C./5 mbar) and the compound was purified by bulb-to-bulb distillation (80° C./0.012 mbar). 40 g of the desired product were obtained (0.23 mol, 82%), as a 2:3 mixture of diastereoisomers.

$^{13}$C-NMR: 204.41 (d), 204.07 (d), 141.41 (s), 140.86 (s), 139.07 (d), 138.11 (d), 128.78 (d), 128.72 (d), 128.35 (d), 128.08 (d), 127.82 (d), 126.82 (d), 116.85 (t), 116.30 (t), 51.45 (d), 51.42 (d), 50.47 (d), 50.37 (d), 12.51 (q), 11.91 (q).

$^1$H-NMR: 9.68 (d, J=2.5, 0.4H), 9.53 (d, J=2.5, 0.6H), 7.32-7.15 (m, 5H), 6.06-5.91 (m, 1H), 5.15-5.06 (m, 2H), 3.58 (t, J=7, 0.6H), 3.52 (t, J=7, 0.4H), 2.83-2.73 (m, 1H), 1.10 (d, J=7, 1.2H), 0.90 (d, J=7, 0.8H).

(1E)-1-[3-(allyloxy)-1-propenyl]-2-methoxybenzene

Prepared as described for (1E)-3-(2'-Butenyloxy)-1-phenyl-1-propene, with the following reagents:
o-methoxycinnamyl alcohol (39 g; 0.23 mol)
Sodium hydride (55% in mineral oil; 20 g; 0.48 mol)
35.35 g of the desired compound were obtained (35.35 g; 0.173 mol; 74%).
B.p.=121° C./0.058 mbar $^{13}$C-NMR: 156.75 (s); 134.89 (d); 128.71 (d); 127.54 (d); 127.00 (d); 126.66 (d); 125.74 (s); 120.62 (d); 116.99 (t); 110.81 (d); 71.28 (t); 70.98 (t); 55.39 (q)

$^1$H-NMR: 7.43 (m, 1H); 7.20 (m, 1H); 6.95-6.82 (m, 3H); 6.30 (m, 1H); 5.94 (m, 1H); 5.30 (m, 1H); 5.18 (m, 1H); 4.15 (m, 2H); 4.02 (m, 2H); 3.82 (s, 3H)

3-(2-methoxyphenyl)-2-methyl-4-pentenal

Prepared as described for compound 2,4-dimethyl-3-(4-methylphenyl)-4-pentenal, with the following reagents:
(1E)-1-[3-(allyloxy)-1-propenyl]-2-methoxybenzene (35.35 g; 0.173 mol)
RuCl$_2$(PPh$_3$)$_2$ (0.02 g)
Pseudo-cumene (72 ml)
32.1 g of the desired product were obtained as a 1:1 mixture of diastereoisomers (0.157 mol; yield=91%).
B.p.=88° C./0.7 mbar $^{13}$C-NMR: 204.97 (s); 204.59 (s); 156.98 (s); 156.50 (s); 138.58 (d); 137.51 (d); 129.68 (s); 129.02 (s); 128.99 (d); 128.74 (d); 127.86 (d); 127.84 (d); 120.77 (d); 120.72 (d); 116.83 (t); 116.26 (t); 110.82 (d); 55.27 (q); 49.43 (d); 49.40 (d); 45.13 (d); 44.87 (d); 12.01 (q); 11.80 (q)

$^1$H-NMR: 9.68 (d, J=3.5 Hz, 0.5H); 9.50 (d, J=7 Hz, 0.5H); 7.23-7.10 (m, 2H); 6.93-6.82 (m, 2H); 6.13-6.00 (m, 1H); 5.15-5.08 (m, 2H); 4.02-3.94 (m, 1H); 3.84 (s, 1.5H); 3.82 (s, 1.5H); 2.92-2.80 (m, 1H); 1.08 (d, J=7 Hz, 1.5H); 0.88 (d, J=7 Hz, 1.5H)

4-methyl-3-phenyl-4-pentenenitrile

4-Methyl-3-phenyl-4-pentenal (15.27 g; 0.077 mol) and hydroxylamine hydrochloride (8.1 g; 0.116 mol) were heated together in 95% ethyl alcohol (125 ml) at reflux under nitrogen for 3 hours. Ethyl alcohol was removed on the rotavapor and the residue partitioned between n-heptane and water (100 ml each). The aqueous phase was reextracted with n-heptane (100 ml). Each organic phase was washed with 5% aqueous HCl, water, aqueous saturated NaHCO$_3$ and brine (100 ml each). Combined extracts were dried over anhydrous sodium sulfate. The product was purified by column chromatography on silica gel (eluting with heptane/ethyl acetate 10:1 to 5:1) followed by bulb-to-bulb distillation. 4.9 g of the desired product were obtained (0.0285 mol; yield=37%).
B.p.=71° C./0.001 mbar $^{13}$C-NMR: 144.41 (s); 139.81 (s); 128.83 (d); 127.57 (d); 127.47 (d); 118.57 (s); 111.92 (t); 48.60 (d); 22.63 (t); 21.49 (q)

$^1$H-NMR: 7.36-7.18 (m, 5H); 5.03 (b.s, 1H); 4.96 (b.s, 1H); 3.58 (t, J=7 Hz, 1H); 2.75 (m, 2H); 1.62 (s, 3H)

4-methyl-3-(4-methylphenyl)-4-pentenenitrile

Same procedure as for 4-methyl-3-phenyl-4-pentenenitrile, using the following reagents:
4-Methyl-3-(4-methylphenyl)-4-pentenal (8.3 g; 0.044 mol)
Hydroxylamine hydrochloride (4.6 g; 0.066 mol)
5.05 g of the desired product were obtained (0.027 mol; yield=62%).
B.p.=80° C./0.001 mbar
$^{13}$C-NMR: 144.62 (s); 137.19 (s); 136.82 (s); 129.50 (d); 127.33 (d); 118.66 (s); 111.70 (t); 48.25 (d); 22.71 (t); 21.48 (q); 21.03 (q)
$^1$H-NMR: 7.16-7.08 (m, 4H); 5.02 (b.s, 1H); 4.95 (b.s, 1H); 3.55 (t, J=7 Hz, 1H); 2.73 (m, 2H); 2.32 (s, 3H); 1.62 (s, 3H)

Example 2

Preparation of a Perfuming Composition

An eau de cologne for man, of the musky-herbaceous type, was prepared by admixing the following ingredients:

| Ingredient | Parts by weight |
|---|---|
| Carbinol acetate | 50 |
| 10* Cis-3-Hexenol acetate | 20 |
| Citronellyl acetate | 20 |
| Linalyl acetate | 350 |
| 10%* Isoeugenyl acetate | 40 |
| 16-Hexadecanolide | 10 |
| 10%* Methyl anthranilate | 40 |
| Cetalox ®[1] | 10 |
| 10%* Cis-3-Hexenol | 20 |
| 10%* Citral | 30 |
| Coumarine | 10 |
| 10%* Damascone Alpha | 20 |
| Dihydromyrcenol | 400 |
| 10%* Damascone Beta | 20 |
| Floralozone[2] | 25 |
| 70%** Galaxolide ®[3] | 600 |
| Geranium essential oil | 5 |
| Hedione ®[4] HC | 160 |
| Helvetolide ®[5] | 80 |
| Iso E Super ®[6] | 200 |
| Lavender essential oil | 50 |
| Lilial ®[7] | 200 |
| 10%* Methylnaphtylcetone | 20 |
| Mousse Cristal | 40 |
| Romandolide ®[8] | 500 |
| Amyl salicylate | 60 |
| Benzyl salicylate | 100 |
| Cis-3-Hexenol salicylate | 200 |
| Tonalide ®[9] | 200 |
| 10%* 2,4-Dimethyl-3-cyclohexene-1-carbaldehyde | 20 |
| | 3500 |

*in dipropyleneglycol
**in isopropyle myristate
[1] 8,12-epoxy-13,14,15,16-tetranorlabdane; origin: Firmenich SA, Geneva, Switzerland
[2] 3-(4/2-ethylphenyl)-2,2-dimethylpropanal; origin: International Flavors & Fragrances, USA
[3] 1,3,4,6,7,8-hexahydro-4,6,6,7,8,8-hexamethyl-cyclopenta-g-2-benzopyrane; origin: International Flavors & Fragrances, USA
[4] methyl cis-dihydrojasmonate; origin: Firmenich SA, Geneva, Switzerland
[5] (1S,1'R)-2-[1-(3',3'-dimethyl-1'-cyclohexyl)ethoxy]-2-methylpropyl propanoate; origin: Firmenich SA, Geneva, Switzerland
[6] 1-(octahydro-2,3,8,8-tetramethyl-2-naphthalenyl)-1-ethanone; origin: International Flavors & Fragrances, USA
[7] 3-(4-tert-butylphenyl)-2-methylpropanal; origin: Givaudan SA, Geneva, Switzerland
[8] (1S,1'R)-[1-(3',3'-dimethyl-1'-cyclohexyl)ethoxycarbonyl]methyl propanoate; origin: Firmenich SA, Geneva, Switzerland
[9] (5,6,7,8-tetrahydro-3,5,5,6,8,8-hexamethyl-2-naphthyl)-1-ethanone; origin: Givaudan SA, Geneva, Switzerland The addition of 200 parts by weight of 2,4-dimethyl-3-(4-methylphenyl)-4-pentenal to the above-described eau de cologne imparted to the latter an anis connotation and reinforced the herbaceous character by providing a basil touch.

Example 3

Preparation of a Perfuming Composition

A cologne, of the floral-watery type, was prepared by admixing the following ingredients:

| Ingredient | Parts by weight |
|---|---|
| 10%* Phenylacetic aldehyde | 20 |
| 16-Hexadecanolide | 40 |
| Dihydro Beta Ionone | 350 |
| 7-Methyl-2H,4H-1,5-benzodioxepin-3-one | 80 |
| Citronellol | 300 |
| Allyl (cyclohexyloxy)-acetate | 20 |
| Decal | 20 |
| Dimetol ®[1] | 20 |
| 10%* Ethylvanilline | 100 |
| Eugenol | 80 |
| Exaltolide ®[2] | 360 |
| 70%** Galaxolide ®[3] | 2200 |
| Hedione ®[4] | 1000 |
| 10%* Indol | 150 |
| Beta Ionone | 20 |
| Iso E Super ®[5] | 1300 |
| Lilial ®[6] | 1150 |
| Linalool | 270 |
| Lyral ®[7] | 250 |
| 10%* 2,6-Dimethyl-5-heptanal | 50 |
| Paradisone ®[8] | 100 |
| Phenethylol | 70 |
| 10%* 2,4-Dimethyl-3-cyclohexene-1-carbaldehyde | 50 |
| | 8000 |

*in dipropyleneglycol
**in isopropyle myristate
[1] 2,6-dimethyl-2-heptanol; origin: Givaudan SA, Geneva, Switzerland
[2] pentadecanolide; origin: Firmenich SA, Geneva, Switzerland
[3] 1,3,4,6,7,8-hexahydro-4,6,6,7,8,8-hexamethyl-cyclopenta-g-2-benzopyrane; origin: International Flavors & Fragrances, USA
[4] methyl dihydrojasmonate; origin: Firmenich SA, Geneva, Switzerland
[5] 1-(Octahydro-2,3,8,8-tetramethyl-2-naphthalenyl)-1-ethanone; origin: International Flavors & Fragrances, USA
[6] 3-(4-tert-butylphenyl)-2-methylpropanal; origin: Givaudan SA, Geneva, Switzerland
[7] 4/3-(4-hydroxy-4-methylpentyl)-3-cyclohexene-1-carbaldehyde; origin: International Flavors & Fragrances, USA
[8] (+)-methyl (1R)-cis-3-oxo-2-pentyl-1-cyclopentaneacetate; origin: Givaudan SA, Geneva, Switzerland The addition of 300 parts by weight of 2,4-dimethyl-3-(4-methylphenyl)-4-pentenal to the above-described eau de cologne imparted to the latter a nice powdery-anis aspect comprising a fruity-apple note.

Example 4

Preparation of a Perfuming Composition

A perfuming composition for a fabric softener was prepared by admixing the following ingredients:

| Ingredient | Parts by weight |
|---|---|
| Benzyl acetate | 150 |
| Carbinol acetate | 50 |
| Anis aldehyde | 80 |
| 10%* C 12 Aldehyde | 40 |
| 10%* C 8 Aldehyde | 20 |
| Hexylcinnamic aldehyde | 150 |
| 10%* MNA Aldehyde | 30 |
| Methyl anthranilate | 40 |

-continued

| Ingredient | Parts by weight |
|---|---|
| 10%* Ethyl 2-methylpentanoate | 40 |
| Undecalactone Gamma | 50 |
| Benzophenone | 10 |
| Cetalox ®[1) | 40 |
| Lemon essential oil | 50 |
| Citronellol | 150 |
| 4-Cyclohexyl-2-methyl-2-butanol | 220 |
| Verdyl propionate | 100 |
| Coumarine | 150 |
| 3-(4-Isopropylphenyl)-2-methylpropanal | 20 |
| Damascone Alpha | 10 |
| (1'R,E)-2-Ethyl-4-(2',2',3'-trimethyl-3'-cyclopenten-1'-yl)-2-buten-1-ol[2) | 50 |
| Dihydromyrcenol | 120 |
| Ethylvanilline | 20 |
| Habanolide ®[3) | 100 |
| Heliotropine | 50 |
| Iralia ®[4) Total | 120 |
| Lilial ®[5) | 200 |
| Isopropyl methylbutyrate | 10 |
| Methylnaphthylketone | 30 |
| 10%* Mousse Cristal | 60 |
| Muscenone6[5) Delta | 20 |
| Hedione ®[7) | 250 |
| 10%* Neobutenone ®[8) Alpha | 10 |
| Nirvanol ®[9) | 30 |
| Patchouli essential oil | 20 |
| Peonile ®[10) | 200 |
| Phenethylol | 250 |
| Phenylhexanol | 450 |
| Orange essential oil | 50 |
| Hexyle salicylate | 50 |
| Benzyl salicylate | 200 |
| Terpineol | 50 |
| Tetralinol | 200 |
| Undecavertol | 20 |
| Yara Yara | 20 |
| 2,4-Dimethyl-3-cyclohexene-1-carbaldehyde | 20 |
| | 4000 |

*in dipropyleneglycol
[1)8,12-epoxy-13,14,15,16-tetranorlabdane; origin: Firmenich SA, Geneva, Switzerland
[2)origin: Firmenich SA, Geneva, Switzerland
[3)pentadecanolide; origin: Firmenich SA, Geneva, Switzerland
[4)mixture of methyl ionones; origin: Firmenich SA, Switzerland
[5)3-(4-tert-butylphenyl)-2-methylpropanal; origin: Givaudan-Roure SA, Vernier, Switzerland
[6)3-methyl-(4)-cyclopentadecenone; origin: Firmenich SA, Switzerland
[7)methyl dihydrojasmonate; origin: Firmenich SA, Switzerland
[8)1-(5,5-dimethyl-1-cyclohexen-1-yl)-4-penten-1-one; origin: Firmenich SA, Switzerland
[9)3,3-dimethyl-5-(2,2,3-trimethyl-3-cyclopenten-1-yl)-4-penten-2-ol; origin: Firmenich SA, Switzerland
[10)Cyclohexylidene(phenyl)acetonitrile; origin: Givaudan-Roure SA, Vernier, Switzerland When there were added 100 parts by weight of 2,4-dimethyl-3-(4-methylphenyl)-4-pentenal to the above-described perfume, then the new fragrance acquired a powdery-anis sweetness different from the one obtained when instead of the invention's compound it was used the same amount of Anis aldehyde, 3-(4-methoxyphenyl)-2-methylpropanal or 3-(1,3-benzodioxol-5-yl)-2-methylpropanal (compounds known to impart similar odor note). Indeed the invention's compound provided a note more aldehydic and floral, as well as on a dry or wet fabric.

What is claimed is:

1. A method to confer, enhance, improve or modify the odor properties of a perfuming composition or of a perfumed article, which method comprises adding to the composition or article an effective amount of at least one compound of formula

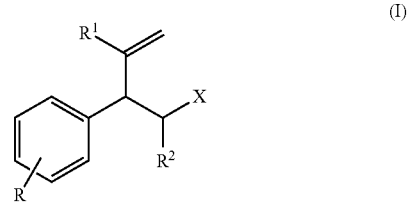

to provide floral and/or green odor notes, wherein:
R is an ortho, meta or para substituent of the phenyl ring and is methyl or ethyl group;
$R^1$ is a methyl or ethyl group;
$R^2$ is a hydrogen atom or a methyl or ethyl group; and
X is a CHO.

2. The method according to claim 1, wherein the R group is a methyl or ethyl group.

3. The method according to claim 1, wherein the compound is 2,4-dimethyl-3-(4-methylphenyl)-4-pentenal, or 4-methyl-3-(4-methylphenyl)-4-pentenal.

4. The method according to claim 1, wherein the compound is present in a perfuming composition that includes at least one ingredient selected from the group consisting of a perfumery carrier and a perfumery base; and optionally at least one perfumery adjuvant.

5. The method according to claim 4, wherein the compound is 2,4-dimethyl-3-(4-methylphenyl)-4-pentenal, or 4-methyl-3-(4-methylphenyl)-4-pentenal.

6. The method according to claim 1, wherein the compound is present in a perfumed article comprising that includes a consumer product base.

7. The method according to claim 6, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

8. The method according to claim 6, wherein the compound is 2,4-dimethyl-3-(4-methylphenyl)-4-pentenal, or 4-methyl-3-(4-methylphenyl)-4-pentenal.

* * * * *

UNITED STATES PATENT AND TRADEMARK OFFICE
CERTIFICATE OF CORRECTION

PATENT NO. : 8,268,895 B2  Page 1 of 1
APPLICATION NO. : 13/123147
DATED : September 18, 2012
INVENTOR(S) : Moretti It is certified that error appears in the above-identified patent and that said Letters Patent is hereby corrected as shown below:

Title Page:
Item (56), References Cited, OTHER PUBLICATIONS, Gladiali et al. reference, change "$H_4Ru_4(CO)_8[(-31)-DIOP]_2$," to -- $H_4Ru_4(CO)_8[(-)-DIOP]_2$, --.

Column 16:
Line 41 (claim 6, line 2), after "comprising", delete "that includes".

Signed and Sealed this
Thirtieth Day of October, 2012

David J. Kappos
*Director of the United States Patent and Trademark Office*